United States Patent [19]

Narayanan et al.

[11] Patent Number: 5,336,518
[45] Date of Patent: Aug. 9, 1994

[54] TREATMENT OF METALLIC SURFACES USING RADIOFREQUENCY PLASMA DEPOSITION AND CHEMICAL ATTACHMENT OF BIOACTIVE AGENTS

[75] Inventors: Pallassana V. Narayanan, Davie; Stephen M. Rowland; Kimberly D. Stanley, both of Miami, all of Fla.

[73] Assignee: Cordis Corporation, Miami Lakes, Fla.

[21] Appl. No.: 989,105

[22] Filed: Dec. 11, 1992

[51] Int. Cl.$^5$ .................... A61F 2/00; A61M 23/00
[52] U.S. Cl. ........................... 623/1; 427/470; 427/2.25; 424/422; 424/423; 530/815; 530/816
[58] Field of Search ............... 427/2, 490; 604/264, 604/265, 267; 530/402, 811, 812, 815, 816; 424/422, 423

[56] References Cited

U.S. PATENT DOCUMENTS

| | | | |
|---|---|---|---|
| 3,549,409 | 12/1970 | Dyck | 117/47 |
| 3,639,141 | 2/1972 | Dyck | 117/47 A |
| 3,826,678 | 7/1974 | Hoffman et al. | 117/81 |
| 4,378,435 | 3/1983 | Takagi et al. | 435/180 |
| 4,521,564 | 6/1985 | Solomon | 525/54.1 |
| 4,634,762 | 1/1987 | Feijen et al. | 530/350 |
| 5,034,265 | 6/1991 | Hoffmann et al. | 428/253 |
| 5,100,689 | 3/1992 | Goldberg et al. | 427/2 |

FOREIGN PATENT DOCUMENTS 1583008 10/1977 United Kingdom .

OTHER PUBLICATIONS

C. Reilly et al., Heparin Prevents Vascular Smooth Muscle Cell Progression Through The G$_1$ Phase Of The Cell Cycle, The Journal of Biological Chemistry, vol. 264, No. 12 (Apr. 25, 1989) pp. 6990–6995.

E. Edelman et al., Effect Controlled Advestitial Heparin Delivery On Smooth Muscle Cell Proliferation Following Endothelian Injury Proc. Natl. Acad, Sci, USA, vol. 87 (May, 1990), pp. 3773–3776.

A. Clowes et al., Kinetics of Cellular Proliferation After Arterial Injury, II. Inhibition of Smooth Muscle Growth by Heparin Laboratory Investigation, vol. 52, No. 6 (1985), pp. 611–616.

R. Majack & P. Bornstein, Regulation of Collagen Biosynthesis, Part III Collagen Biosynthesis, pp. 172–179 (1985).

H. Hartmut et al., Inhibition of Cellular Proliferation After Experimental Balloon Angioplasty by Low-Molecular-Weight Heparin, Circulation, vol. 85, No. 4, Apr. 1992, pp. 1548–1556.

H. Wessel et al., Heparin Carboxyl-Reduced Sulfated Heparin and Trestatin A. Sulfate, Anti-proliferative and anti-coagulative activities Carbohydrate Research, 204, (1990) pp. 131–139.

P. D'Amore et al., Heparin-Endothelial Cell Interactions Haemostasis 1990; 20 (Suppl. 1): 159–165.

L. Striker et al., Biology of Disease, Mesangial Cell Turnover: Effect of Heparin and Peptide Growth Factors, Laboratory Investigation vol. 64 No. 4, pp. 446–456, 1991.

(List continued on next page.)

*Primary Examiner*—Asok Pal
*Assistant Examiner*—P. Achutamurthy
*Attorney, Agent, or Firm*—Lockwood, Alex, FitzGibbon & Cummings

[57] ABSTRACT

A treatment for metallic surfaces and devices having metallic surfaces is described. A film of heptafluorobutylmethacrylate (HFBMA) is applied to a surface by radiofrequency (RF) plasma deposition and subsequently treated with a biologically active agent. A water vapor RF plasma treatment of the HFBMA coating provides reactive groups thereon which can covalently bond to the biologically active agent. Alternatively, a spacer group can be bonded to the activated HFBMA and the biologically active agent can then be bonded to the spacer group. Devices coated according to the invention possess enhanced biocompatibility and the HFBMA coatings are durable even under severe crimping and expansion conditions.

16 Claims, 1 Drawing Sheet

OTHER PUBLICATIONS

Nagasaki et al., Heparin Potentiates the Action of Plasma Membrane–Associated Growth Stimulatory Activity Journal of Cellular Physiology, 133: 365–371 (1987).

Currier et al., Low Molecular Weight Heparin (Enoxaprin) Reduces Restenosis After Iliac Angioplasty in the Hypercholesterolemic Rabbit JACC vol. 17 No. 6, May 1991: 118B–25B.

J. Ip et al., The Role of Platelets, Thrombin in Hyperplasia and Restenosis After Coronary Angioplasty JACC vol. 17, No. 6, May 1991: 77B–88B.

Berk et al., Pharmacologic Roles of Heparin and Glucocorticoids to Prevent Restenosis After Coronary Angioplasty JACC vol. 17, No. 6, May, 1991: 111B–7.

Betz, Cell Culture Systems to Study Progression Inhibition of Intimal Proliferations Basic Res. Cardiol. 86: 79–86 (1991).

TREATMENT OF METALLIC SURFACES USING RADIOFREQUENCY PLASMA DEPOSITION AND CHEMICAL ATTACHMENT OF BIOACTIVE AGENTS

BACKGROUND AND BRIEF DESCRIPTION OF THE INVENTION

The present invention generally relates to the treatment of metallic surfaces to enhance their biocompatibility and to medical devices and the like which include such biocompatible surfaces. More specifically, the invention relates to depositing a film of heptafluorobutylmethacrylate ("HFBMA") on a metallic surface using radiofrequency plasma deposition and subsequently functionalizing the deposited HFBMA by a water vapor radiofrequency plasma treatment. Biologically active agents are bound to the HFBMA coated surface so that medical devices which include such surfaces possess an improved biocompatibility.

Those skilled in the art will appreciate the importance of certain medical devices having surfaces of an enhanced biocompatibility. Medical devices made from polymeric materials as well as from metallic materials generally benefit from having enhanced biocompatibility especially where such devices are intended for subcutaneous implantation where they can experience in vivo environments depending on the nature of the particular device. The biocompatibility of such medical devices is generally enhanced by attempting to secure certain agents to the surface of those devices. For example, anti-thrombogenic agents are often secured to the surfaces of medical devices having blood contacting surfaces. It would be particularly undesirable to have the anti-thrombogenic agent leach away in wet environments such as those encountered by medical devices that engage blood or other body fluids.

Attempts have been made and approaches have been suggested for activating the surface of a medical device with a radiofrequency ("RF") plasma. The activated surface reacts with heparin or other biologically active agents to provide a biocompatible surface having specific characteristics such as Anti-thrombogenicity, endothelial growth promoters, and the like. The treatment of surfaces with a radiofrequency plasma has been described in various patents. Included are patents incorporating plasma discharge treatment with a gaseous environment including a variety of gases such as inert and organic gases. Patents in this regard include U.S. Pat. Nos. 4,613,517, 4,656,083 and 4,948,628, which mention a variety of plasma media including those generated from hydrogen, helium, ammonia, nitrogen, oxygen, neon, argon, krypton, xenon, ethylenic monomers and other hydrocarbons, halohydrocarbons, halocarbons and silanes. Certain of these plasma media are relatively expensive and can be hazardous to use within a manufacturing environment and/or to dispose of as waste. Certain plasma media are more suitable for treatment of specific substances.

Other surface treatments have been proposed specifically for metal surfaces intended to contact bodily fluids and the like during implantation. One such treatment involves the chemical oxidation of the metallic surface, such as a tantalum surface, until enough of a metal oxide layer is provided for bonding with a bioactive agent. Many other approaches in this area have concentrated on utilizing polymeric surfaces as the surface which encounters the body fluids and then treating those polymeric surfaces according to a variety of procedures. Polymeric surfaces and metallic surfaces each pose different problems which must be overcome to provide a polymeric or metallic surface that is suitable for implantation and/or extended-time residence within the body. U.S. Pat. Nos. 3,549,409 and 3,639,141 describe treatments of particular polymeric surfaces by swelling the polymeric surface, bonding an agent thereto and noncovalently coupling heparin to that agent. The latter of these patents mentions contacting the polymeric surface with an amino alkyl trialkoxysilane dissolved in an organic solvent to swell the polymeric material. Another approach involving a chemical treatment is exemplified by U.S. Pat. Nos. 4,526,714 and 4,634,762 which indicate that a surface can be rendered biocompatible by coating it with a conjugate of heparinous material and a protein, with the conjugate being formed by coupling carried out in the presence of 1-ethyl-3-dimethyl-aminopropyl carbodiimide (known as EDC) and the like as a coupling agent. The conjugate is attached to the substrate surface at the sites where the surface free functional groups suitable for bonding to the conjugate are present. In order to effect the coupling needed to form this conjugate, these free functional groups on the substrate surface are provided as free amino groups.

Another treatment procedure involves treatment of a surface with heparin benzalkonium chloride (HBAC). A quaternary amine structure is involved. The result is an ionic linkage, and subsequent ionic exchange occurs quite readily. For example, HBAC is easily leached from the treated surfaces to the extent that substantially all of the heparin is removed within about three days under leaching conditions. In addition, 4M guanidine, which is used to demonstrate the ionic nature of bonds by an ionic exchange mechanism, quickly removes the heparin in a one hour, non-physiological ionic release test. Furthermore, because benzalkonium chloride is in essence a surfactant, an HBAC conjugated surface is a cytotoxic material as well as a hemolytic material, causing a breakdown of red blood cells.

Other quaternary amine alternatives are believed to be non-hemolytic such as tetradodecylammonium chloride (TDAMC), for example. These types of materials are typically applied from a hydrocarbon solvent system, also providing ionic bonding and ionic exchange can and does occur quite readily. Because of its molecular structure, heparin and materials having similar functions do not escape quite as readily from TDAMC as from HBAC, but leaching is still very apparent. When attachment to a surface is by means of ionic bonding of TDAMC and the like, most of the heparin or bioactive agent is leached away after three hours of contact with blood plasma or after about 24 hours within a phosphate buffered saline solution under physiological conditions. The ionically attached material is substantially completely removed with guanidine within about one hour during non-physiological testing.

Many of the above-discussed attempts to improve the biocompatibility of various medical devices do not fare well under in vivo or biological conditions, and they fall short of fulfilling desirable attributes such as having the coating remain functional for a length of time adequate to provide maximum thrombus prevention. Another important consideration is whether the coating interferes with endothelialization. For metallic medical devices which undergo movements, such as bending of a portion thereof during implantation and/or use, the mechanical properties of the treatment coating should be able to withstand flexure during bending, expansion and the like of the coated member. For example, metallic radially expandable generally tubularly shaped endoprostheses which are generally known as stents, must be able to withstand such flexure. An exemplary stent is described in U.S. Pat. No. 5,019,090, the subject matter thereof being incorporated by reference hereinto. Such stents are made of a very fine gauge metallic wire, typically tantalum or stainless steel wire. During implantation, these stents are mounted onto the balloon of an angioplasty catheter or the like until a partially occluded location within the blood vessel is reached, at which time the balloon and the stent are radially and circumferentially expanded for purposes of opening the occlusion and supporting the vessel at that location. This necessarily involves rather extensive bending of the tantalum wire. Many previously available coatings do not have the flexibility and/or adherence properties needed to avoid cracking and/or loss of the coating when subjected to this type of flexure.

It would be desirable to design and utilize a system which meets the objectives of imparting biocompatibility to a metallic substrate to thereby substantially prevent thrombus formation on the metallic surface. Such a system should not crack or otherwise deteriorate due to mechanical movement of the treated metallic member and the system should not allow substantial leaching of the biologically active material and should not substantially interfere with endothelialization after in vivo implantation.

It has been determined that a system providing covalent linkages between a bioactive agent and a functionalized HFBMA coated metal surface meets these objectives, providing an enhanced metallic surface with permanently improved biocompatibility. Such a system includes treating a metallic surface of the medical device with an RF plasma to deposit a film of HFBMA and subsequently functionalizing the deposited film by water vapor plasma treatment, thus providing available carboxy and hydroxy groups on the HFBMA coating to facilitate bonding with bioactive agents. The bioactive agents can be bound to the HFBMA surface using different reaction schemes and reagents including without limitation carbodiimide chemistry, organosilane chemistry, Woodwards K reagent and glutaraldehyde cross-linking. Various anti-thrombogenic agents, endothelial growth promoters, smooth muscle cell anti-proliferative agents, platelet growth factor antagonists, vasoconstrictors and vasodialators and cellular adhesion promoters can all be applied alone or in combination with spacers such as albumin, polyethylene oxide, various diacid chlorides, polyethyleneimine, N-(2-aminoethyl-3-aminopropyl) trimethoxysilane and the like.

The activated HFBMA-modified metallic surface may be treated with either a spacer or the bioactive agent using carbodiimide chemistry utilizing a water soluble carbodiimide. The molecule attached to the surface (either the HFBMA or the spacer) must have a primary or secondary amine and for a spacer there must be at least two primary or secondary amines. Endovascular stents can be made using these HFBMA coated metallic surfaces. There is evidence to show that a completely and quickly endothelialized object, such as a stent, does not promote smooth muscle cell proliferation and therefore could prevent restenosis.

It is accordingly a general object of the present invention to provide an improved biocompatible metallic surface, a method of preparing such a surface and a method of implanting a device having such a surface.

Another object of the present invention is to provide an improved stent or other medical device having a HFBMA coating which is capable of covalently bonding to bioactive agents and is able to withstand flexure and interaction with fluids.

Another object of this invention is to provide a method for depositing a film of HFBMA by radiofrequency plasma deposition and binding a bioactive agent thereto to provide an enhanced metallic surface with permanently improved biocompatibility.

Another object of the present invention is to provide an improved metallic surface which is particularly compatible and exhibits advantageous properties conducive to long-term placement within a body.

Another object of the present invention is to provide a treatment for metallic surfaces without detrimentally affecting the mechanical properties of the metal.

These and other objects, features and advantages of the present invention will be clearly understood by those skilled in the art through a consideration of the remainder of the disclosure, including the drawings and the detailed description of the preferred embodiments.

DETAILED DESCRIPTION OF THE PREFERRED EMBODIMENTS

The present invention provides an improved biocompatible metallic surface for medical devices and the like by RF plasma deposition of HFBMA over the metallic surface followed by a suitable treatment with a biologically active agent. The resulting surface and/or device shows a permanently improved biocompatibility for in vivo use such as for endovascular stents and the like.

A metallic surface to be treated in accordance with the principles of the present invention is first coated with a film of HFBMA by RF plasma deposition and subsequently functionalized by water vapor RF plasma treatment to provide reactive carboxy and hydroxy groups to facilitate the subsequent bonding of the biologically active agent thereto. The modified HFBMA surface may be treated with either a spacer or bioactive agent having a primary or secondary amine and for a spacer molecule there should be at least two primary or secondary amines to form a covalent bond between the carboxy group of the activated HFBMA and the amine on the spacer or bioactive molecule. The reaction between the HFBMA and the bioactive agent typically proceeds by a condensation reaction or peptide bond formation using a carbodiimide coupling agent to form a covalent bond between the carboxy group of the activated HFBMA and the amine of the bioactive agent.

Although carbodiimide chemistry is one mechanism by which the HFBMA and the bioactive agent are covalently bonded, different reaction schemes and reagents will also produce the desired result. Such schemes and reagents include without limitation organosilane chemistry, Woodwards K reagent as well as glutaraldehyde cross-linking. Numerous bioactive agents can be used in practicing the invention including anti-thrombogenic agents such as heparins, hirudin, hyaluronic acid and PPACK (D-phenylalanyl-L-prolyl-L-arginine chloromethyl ketone); endothelial growth promotors such as vascular endothelial growth factor, gelatin, fibronectin, collagen, laminin, matrigel, and victronectin; smooth muscle cell anti-proliferative agents such as anti-$\beta$-FGF, meulinolin, enoxaparin and 5-fluorouracil; platelet growth factor antagonist; vasoconstrictors and vasodilators; and cellular adhesion promoters.

While the bioactive agents may be applied directly to the HFMBA coating, it may be desirable to first attach a spacer group prior to treating the surface with the bioactive agent. Suitable spacer groups include albumin, polyethyleneimine and N-(2-aminoethyl--3-aminopropyl) trimethoxysilane. Where the bioactive molecule is bound through an organosilane spacer molecule, the reaction is a condensation reaction between the hydroxy groups on the HFBMA coating and the silane functionality on the organosilane. The bioactive molecule is subsequently bound to the amine of the silane by carbodiimide chemistry.

Figure 1:
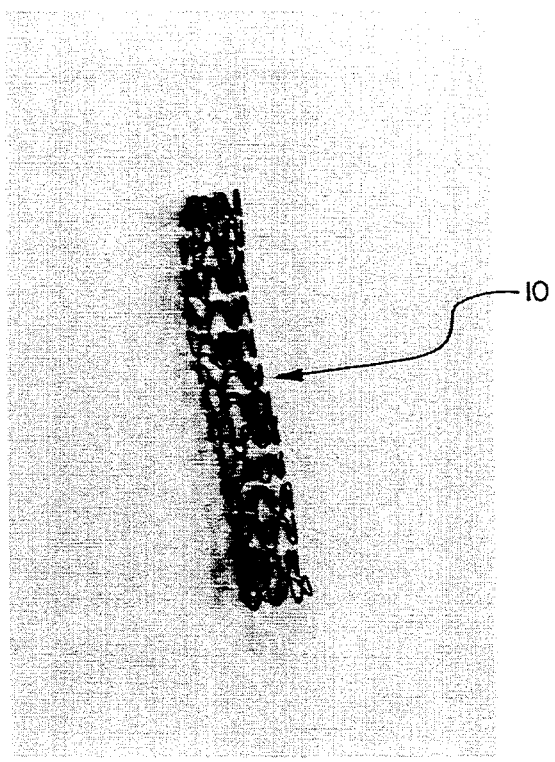
FIG. 1 is a reproduction of a photograph of a stent having an activated HFBMA coating with a covalently bonded heparin coating.

While virtually any metallic surface can experience an enhanced biocompatibility by a treatment of the surface in accordance with the principles disclosed herein, for convenience and simplicity the disclosure frequently discusses the application of the invention in the context of treating endovascular stents such as the stent 10 of FIG. 1. Those skilled in the art will understand that the broader teachings of the invention apply to any metallic surface where an enhanced biocompatability is desired.

In coating a metallic surface of a stent or the like with HFBMA, an RF plasma deposition technique is used and the HFBMA coating is subsequently activated using water plasma treatment. In preparing stents by plasma polymerization, stents are mounted on a metal mount and loaded into a one inch diameter, twelve inch long glass reactor tube. The reactor is RF coupled capacitively by external electrodes and the system is pumped down to remove air. Water and oxygen are introduced into the reactor in a three-to-one ratio and the pressure is adjusted to 100 mtorr. Fifty watts of RF is applied to pretreat the stents with a water/oxygen plasma. After pretreatment, the system is pumped down to remove water and oxygen. Nitrogen and HFBMA are next introduced into the reactor while pressure is maintained at 250 mtorr using a pressure controller system. RF power at 20 watts is then applied for 3.5 minutes to obtain a HFBMA coating. The system is again pumped down to remove the residual HFBMA monomer and nitrogen. Water vapor is introduced into the reactor while pressure is controlled at 400 mtorr and RF power at 20 watts is applied to create a water vapor plasma for 45 seconds to modify the polymer coating obtained in the HFBMA treatment step.

Once the HFBMA coating has been deposited and subsequently activated, the activated surface can be treated with either a bioactive agent or a spacer molecule, as discussed herein. Typically, an aqueous solution of the spacer or bioactive agent is applied to the activated HFBMA coating with an amount of a carbodiimide compound to facilitate a condensation or peptide bond formation using the carbodiimide as a coupling agent. As a coupling agent, the carbodiimide will covalently bond to both the carboxy group on the HFBMA and the amine on the spacer molecule or the bioactive agent. An aqueous solution of N-(3-dimethylaminopropyl)-N'-ethylcarbodiimide hydrochloride (EDC) is a suitable coupling agent. Preferably, the EDC concentration on a weight per volume basis is approximately equal and up to twice the concentration of the spacer or the bioactive agent and is typically between about 4.0 mg/ml and about 8.0 mg/ml. Most typically, where heparin is employed as the bioactive agent, a 1:1 ratio of heparin:EDC is desired. A carbodiimide is not required with an organosilane spacer group since a condensation reaction will occur between the hydroxy groups of the activated HFBMA surface and the hydroxy groups of the silane functionality.

Where a spacer molecule is added directly to the HFBMA coating, the stent is typically placed in a solution of the spacer and exposed to the solution for several minutes. Where a spacer such as polyethylenimine (PEI) is used, a PEI concentration of about 1% by weight is generally adequate with the stent being exposed to the solution for about 5 minutes. Other spacers may require different exposure times depending upon the spacer and the concentration thereof. A stent exposed to a solution of albumin at a concentration of 3.33 mg/ml typically requires exposure to the solution for approximately 15 minutes. Following exposure to the spacer solution, the stent is typically rinsed and/or air dried for a suitable period of time and, in the case of silane spacer, the stent may be oven cured at an elevated temperature of between about 100° C. and about 120° C.

The bioactive agent may be added to the spacer in an aqueous or other suitable solution. The addition of heparin to the spacer is typically accomplished by exposing the stent to an aqueous heparin solution for a period of time between about 20 minutes and about 90 minutes. Where carbodiimide chemistry is employed in bonding the heparin with the spacer molecule, EDC is typically added to the heparin solution to facilitate bonding. A heparin concentration of 6.67 mg/ml with an equal concentration of EDC has been suitable. Of course, other bioactive agents can be used such as hyaluronic acid as well as hirudin, for example. Where heparin is the bioactive agent, the presence of the heparin coating on a stent may be confirmed by known techniques such as by extraction in phosphate buffered saline (PBS) followed by rinsing and staining with toluidine blue. A change in the light refraction will indicate that the samples have picked up the purple color of the dye which commonly occurs in the presence of heparin. Staining the treated stents with berberine sulfate, a fluorescent stain, and an examination of the stained stents under a fluorescent microscope will show a yellow glow in the presence of heparin. Fluorescent thrombin-anti-thrombin (TAT) immunoassay is another technique available to determine the presence of biologically active heparin.

Figure 2:
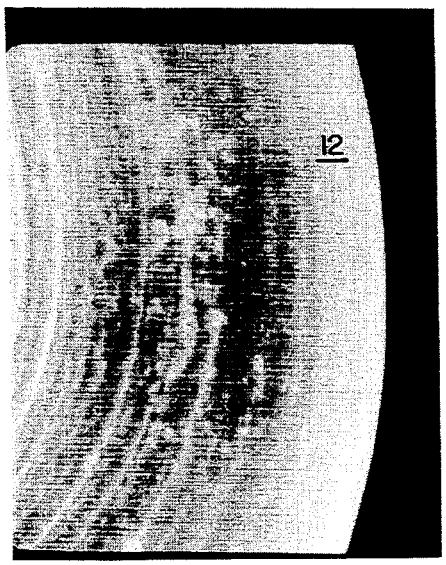
FIGS. 2, 3 are reproductions of SEM photographs of stents which have been treated according to the invention and subjected to canine blood in a closed flow system in which the blood is circulating over the sample for 5 minutes, to determine the blood-material interactions and specifically the effect of the device on the platelets in the blood.
Figure 3:
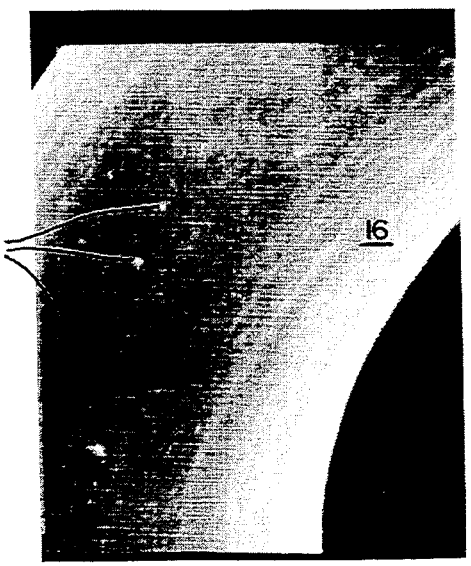

Stents that have been treated according to the invention generally have shown improved durability over stents that have been treated by other techniques to improve their biocompatibility. Coatings of the invention are suitable for deposition on electropolished as well as non-polished metallic surfaces, displaying an improved durability for both surfaces. Non-polished stents, for example, may present at least the potential for irritation of blood vessel lumen due to roughness of non-polished metallic surfaces. The complications can be avoided since the coatings of the present invention will durably adhere to electropolished surfaces. Also, as set forth herein, flow loop analysis performed on stents made in accordance with the invention has demonstrated low platelet activation as well as low platelet adherence, suggesting a reduction in the release of platelet factors which trigger smooth muscle cell migration and phenotypic change. The lack of muscle cell migration would limit the smooth muscle cell proliferation which is one component of the stenosis pathway, suggesting that the coating of the invention may play a part in the prevention of restenosis. Flow loop analysis has shown the coatings of the invention to be generally superior to prior art coatings with no adverse effects on the coagulation system. FIGS. 2 and 3 are illustrative of flow loop data for stents coated according to the invention. The FIGS. 2 and 3 represent SEM photographs, taken at a magnification of 1500× of stents coated with HFBMA-albumin-heparin and subjected to flow loop analysis. The SEM field shown in FIG. 2 reveals no adherent platelets on the stent surface 12, and, the field shown in FIG. 3 reveals only four platelets 14 on the stent surface 16.

The following examples illustrate the inventive biocompatible coatings for metal surfaces and the advantageous properties thereof.

EXAMPLE 1

Stent samples were coated with HFMBA using plasma deposition and the HFBMA coating was activated by water plasma treatment. The coated and activated samples were then treated with an aqueous solution of polyethylenimine (PEI) and EDC with a PEI concentration of 1% by weight and 5 mg/ml EDC at an overall pH of 8. The stent samples were exposed to the PEI:EDC solution for five minutes and were then removed from the solution and rinsed. Heparin was applied from an aqueous solution having a heparin concentration of 6.67 mg/ml with an equal concentration of EDC at an overall pH of 3. The stents were exposed to the heparin for one hour and were then rinsed and air dried. Samples were then extracted in phosphate buffered saline (PBS) for three hours at physiological temperature. The samples were removed and rinsed and then stained with toluidine blue. The light refraction for the samples indicated that the stents had picked up the purple color of the dye, indicating the presence of heparin.

EXAMPLE 2

Stents samples were coated with HFBMA and activated as in Example 1 followed by a treatment with a 2% solution of [3-(2 aminoethyl) aminopropyl] trimethoxysilane for five minutes after which the samples were removed from the solution and air dried for about one minute to remove excess solvent (95% ethanol). The samples were oven cured at 110° C. for ten minutes and then cooled. The stents were exposed to the heparin solution of Example 1 for one hour, and were then rinsed and air dried. The presence of heparin on the stents was confirmed using a PBS extraction as in Example 1.

EXAMPLE 3

Stent samples were treated with HFBMA and activated as in Example 1. Each of the samples were then treated with an aqueous albumin:EDC solution containing 3.33 mg/ml albumin and 6.67 mg/ml EDC. The samples were allowed to sit in the albumin:EDC solution for 15 minutes at a pH of about 5. After fifteen minutes, the samples were removed from the solution and rinsed completely and then placed in a heparin:EDC solution identical to the solution of Example 1. The samples were treated in the heparin solution for thirty minutes and then removed, rinsed and allowed to air dry.

EXAMPLE 4

Stent samples were treated as in Example 3 except that the albumin concentration was 2.5 mg/ml and the EDC concentration was 5mg/ml at an overall pH of about 5. The presence of heparin on the stents was confirmed by PBS extraction as in Example 1. Additionally, a TAT immunoassay was performed on the samples by first incubating the samples in human blood plasma and then rinsing and incubating the samples in a solution of fluorescently labeled anti-thrombin. The stents were examined under fluorescent microscope to confirm the presence of biologically active heparin, as indicated by a yellow glow of the sample surfaces. The biologically active heparin was evenly distributed on the samples. Finally, berberine staining was also performed by staining the stents with fluorescent stain berberine sulfate followed by an examination of the samples under a fluorescent microscope, showing a relatively even yellow glow indicative of the presence of heparin.

EXAMPLE 5

Stents samples which had been electropolished were then treated as in Example 2.

EXAMPLE 6

Stents samples which were previously electropolished were then treated as in Example 4 herein.

EXAMPLE 7

Durability (expansion) testing was conducted on stents prepared according to Examples 1, 2, 4, 5 and 6 to determine the durability of the coating on the stent after the stent had been crimped onto a balloon and then expanded. The analysis was done using a scanning electron microscope (SEM). Results of the examination indicated that although crimping caused some abrasions of the stent coatings, there were no breaks in any of the examined coatings and all of the samples showed a uniform coating covering the entire surface of the stent.

EXAMPLE 8

Flow loop analysis was performed on stent samples prepared as in Examples 4 and 6. This analysis was used to characterize the interaction of platelets with the stent samples. Decalcified blood was passed through a polymethylmethacrylate flow cell containing a stent sample for five minutes. Testing done on the blood both before and after the analysis included activated partial thrombo plastin time (APTT), hemolysis and total blood counts (CBC). Platelet aggregation testing was performed prior to beginning the experiment to determine if the platelets in the blood were acceptable after blood transport to the site of the experiment. Following flow loop analysis, samples were fixed with glutaraldehyde and dehydrated with an ethanol series. SEM analysis was performed to determine the per unit area of platelets adhering to the samples. The samples coated with the HFBMA:albumin:heparin coating on either an electropolished or a non-polished wire exhibited very few platelets adhering to the surface. In some fields, no platelets were observed. The average number of platelets per field was approximately three and platelets that did adhere were observed as spherical and showing little to no signs of activation (e.g. no spreading, cytoplasmic streaming or pseudopod formation was observed). Control samples showed moderate to strong platelet adhesion with the platelets showing signs of activation along with the presence of pseudopods.

EXAMPLE 9

A comparison was made of coated tantalum stents by comparison of flow loop data collected for four stents having various coatings. The data for these stents is presented in Table I. The coated stents included an HFBMA coated stent without a bioactive agent bonded thereto, and another HFBMA coated stent which was further treated to include an albumin spacer group and a heparin coating bonded thereto. A third stent was coated with an aminosilane coating which also included a coating of heparin. A fourth stent was coated with a coating known under the trademark SPI-LON TM, of the Spire Corporation of Bedford, Mass., a polytetrafluoroethylene which is ion-beam sputtered onto the surface of the stent. The control was an uncoated, unpolished tantalum stent.

The aminosilane-heparin coating showed many adherent platelets under SEM examination. The SPI-LON TM coated stent gave very low platelet counts and the two HFBMA-treated stents experienced no adherent platelets in the fields examined by SEM. Additionally, the ability to bond heparin and other bioactive agents to the surface of the HFBMA coating is an advantage over the SPI-LON TM coated stents, enhancing the performance of the device in a targeted area of the body.

TABLE I

| Comparative Flow Loop Data | |
|---|---|
| Stent Coating | Flow Loop (avg. no. platelets/.006 mm$^2$) |
| HFBMA | 0 |
| HFBMA - Albumin-Heparin | 0 |
| Aminosilane-Heparin | 11 |
| SPI-LON TM | 2 |
| (Control) | Massive platelet aggregates on internal diameter of stent |

The above examples illustrate various features of the invention as well as the manner in which devices can be made hereunder. It should now be appreciated that devices, such as the endovascular stents discussed herein, are rendered more biocompatible when coated with the inventive HFBMA/bioactive agent coatings disclosed herein as opposed to prior art coatings. Generally, the coatings of the invention possess improved durability and/or improved biocompatability over other commonly used prior art coatings. For example, the hydrophilic polymer coating known under the trade name HYDROMER TM may satisfactorily endure certain durability testing but typically shows poor hemocompatibility. A xylene-based polymer coating such as PARALENE C TM demonstrates poor hemocompatibility, showing no significant differences from uncoated control samples. Moreover, the PARALENE C TM coating is easily disrupted during durability testing, experiencing plastic deformation and even slight disruption of the coating. Similarly, certain tetrafluoroethylene (TFE) coatings and coatings made from hyaluronic acid will typically experience massive disruption under crimping and expansion testing. The coatings of the present invention, however, are biocompatible while also being very durable.

It will be understood that the embodiments of the present invention which have been described are illustrative of some of the applications of the principles of the present invention. Modifications may be made by those skilled in the art without departing from the true spirit and scope of the invention.

What is claimed is:

1. A method for rendering biocompatible a metal surface of a medical device, comprising the steps of:
    coating said metal surface with a layer of heptafluorobutylmethacrylate monomer to form a polymer coating on said surface;
    treating said polymer coating with water vapor plasma to provide reactive groups thereon; and
    applying a biologically active agent to said polymer coating;
    the thus formed device being a biocompatible metallic member which, when implanted within a blood vessel, prevents substantial thrombus from occurring on its surface while not significantly interfering with endothelialization of said surface.

2. The method of claim 1 wherein the step of treating said polymer coating further includes applying a spacer molecule thereto, said spacer molecule forming a covalent linkage with said polymer coating; and said applying of said biologically active agent is performed after said spacer molecule is applied to said polymer coating, said biologically active agent and said spacer molecule also forming a covalent linkage therebetween.

3. The method of claim 1 wherein the step of coating said metal surface with a layer of heptafluorobutylmethacrylate is accomplished using a radio frequency plasma deposition thereof; and the step of treating said polymer coating by water vapor is also accomplished by a radio frequency plasma treatment of said polymer coating.

4. The method of claim 1 wherein the step of applying a biologically active agent includes exposing the polymer coating to an aqueous heparin solution having a heparin concentration of between about 4.0 mg/ml and about 8.0 mg/ml for a period of between about 30 and about 90 minutes.

5. The method of claim 4 wherein the step of exposing the polymer coating to an aqueous heparin solution is accomplished in the presence of a carbodiimide compound in solution with said heparin and at a concentration approximately equal to the concentration of said heparin.

6. The method of claim 5 wherein said carbodiimide is N-(3-dimethylaminopropyl)-N'-ethylcarbodiimide hydrochloride.

7. The method of claim 2 wherein said spacer molecule is albumin, an alkyleneimine or an alkoxysilane and the step of applying a spacer molecule is accomplished by exposing said polymer coating to a solution of said spacer molecule for a period of between about two minutes and about thirty minutes.

8. The method of claim 7 wherein the step of applying a spacer molecular is accomplished by exposing the polymer coating to an aqueous solution of albumin or polyethyleneimine, said solution also including at least about 5.0 mg/ml of N-(3-dimethylaminopropyl)-N'-ethylcarbodiimide hydrochloride.

9. The method of claim 7 wherein the step of applying a spacer molecule is accomplished by exposing the polymer coating to a solution of trimethoxysilane in 95% ethanol for a period of at least about 3 minutes.

10. A medical device having a biocompatible antithrombogenic metallic surface, comprising:
   a metallic surface having a biologically active treatment adhered thereto;
   said biologically active treatment including a coating of heptafluorobutylmethacrylate polymer having reactive groups thereon, and a biologically active agent covalently bonded to said reactive groups;
   whereby the biocompatible metallic surface, when implanted within a blood vessel, substantially prevents thrombus formation thereon while avoiding any significant interference of the development of endothelialization of the biocompatable metallic surface.

11. The medical device of claim 10 wherein said metallic surface is an endovascular stent.

12. The medical device of claim 10 wherein said biologically active agent is selected from the group consisting essentially of heparins, hirudin, hyaluronic acid, D-phenylalanyl-L-proyl-L-arginine chloromethyl ketone, vascular endothelial growth factor, gelatin, fibronectin, collagen, laminin, matrigel, victronectin, anti-β-FGF, meulinolin, enoxaparin, 5-fluorouracil, platelet growth factor antagonist, vasoconstrictors and vasodilators, and cellular adhesion promotors.

13. A medical device having a biocompatible antithrombogenic metallic surface, comprising:
   a metallic surface with a biologically compatible treatment adhered thereto;
   said biologically active treatment including a heptafluorobutylmethacrylate polymer coating adhered to said metallic surface, a spacer molecule covalently bonded to said polymer coating and a biologically active agent covalently bonded to said spacer molecule;
   whereby, the biocompatible metallic member, when implanted within a blood vessel, prevents substantial thrombus from occurring on its surface while not significantly interfering with endothelialization of said surface.

14. The medical device of claim 13 wherein said metallic surface is an endovascular stent.

15. The medical device of claim 13 wherein said spacer molecule is selected from a group consisting essentially of albumin, polyethyleneimine, and N-(2-aminoethyl-3-aminopropyl) trimethoxysilane.

16. The medical device of claim 13 wherein said biologically active agent is selected from the group consisting essentially of heparins, hirudin, hyaluronic acid, D-phenylalanyl--L-proyl-L-arginine chloromethyl ketone, vascular endothelial growth factor, gelatin, fibronectin, collagen, laminin, matrigel, victronectin, anti-β-FGF, meulinolin, enoxaparin, 5-fluorouracil, platelet growth factor antagonist, vasoconstrictors and vasodilators, and cellular adhesion promotors.

* * * * *

UNITED STATES PATENT AND TRADEMARK OFFICE
CERTIFICATE OF CORRECTION

PATENT NO. : 5,336,518
DATED      : August 9, 1994
INVENTOR(S): Pallassana V. Narayanan, Stephen M. Rowland and Kimberly D. Stanley It is certified that error appears in the above-indentified patent and that said Letters Patent is hereby corrected as shown below:

Col. 1, lines 27-28, "in vivo" should be in italics;
    line 43, "Anti-thrombogenicity" should read
    --anti-thrombogenicity--.
Col. 2, line 62, "in vivo" should be in italics.
Col. 3, line 32, "in vivo" should be in italics.
Col. 4, line 6, "having a" should read --having an--;
    lines 48-49, "in vivo" should be in italics.
Col. 5, lines 22-23, "N-(2-aminoethyl---3-aminopropyl)"
    should read --N-(2-aminoethyl-3-aminopropyl)--;
    line 57, "obtain a" should read --obtain an--.
Col. 8, line 26, "under fluorescent" should read --under
    a fluorescent--.
Col. 11, line 4, "molecular" should read --molecule--;
    line 32, "D-phenylalanyl-L-proyl-L-arginine" should
    read --D-phenylalanyl-L-prolyl-L-arginine--.
Col. 12, line 28, "D-phenylalanyl--L-proyl-L-arginine"
    should read --D-phenylalany_-L-prolyl-L-arginine--.

Signed and Sealed this

Tenth Day of October, 1995

Attest:

BRUCE LEHMAN

Attesting Officer

Commissioner of Patents and Trademarks